(12) United States Patent
Crisler

(10) Patent No.: US 12,138,241 B2
(45) Date of Patent: Nov. 12, 2024

(54) COMPOSITIONS FOR PREVENTING AND TREATING DIABETES

(71) Applicant: Shaman Naturals, LLC, Rock Springs, WY (US)

(72) Inventor: Maria Crisler, Rock Springs, WY (US)

(73) Assignee: SHAMAN NATURALS, LLC, Casper, WY (US)

( * ) Notice: Subject to any disclaimer, the term of this patent is extended or adjusted under 35 U.S.C. 154(b) by 0 days.

(21) Appl. No.: 17/305,510

(22) Filed: Jul. 8, 2021

(65) Prior Publication Data

US 2022/0133683 A1 May 5, 2022

Related U.S. Application Data

(60) Provisional application No. 63/049,406, filed on Jul. 8, 2020.

(51) Int. Cl.
| | | |
|---|---|---|
| *A61K 31/352* | (2006.01) | |
| *A61K 31/05* | (2006.01) | |
| *A61K 31/7048* | (2006.01) | |
| *A61K 45/06* | (2006.01) | |

(52) U.S. Cl.
CPC ............ *A61K 31/352* (2013.01); *A61K 31/05* (2013.01); *A61K 31/7048* (2013.01); *A61K 45/06* (2013.01)

(58) Field of Classification Search
CPC .................. A61K 31/352; A61K 31/05; A61K 31/7048; A61P 3/10
See application file for complete search history.

(56) References Cited

U.S. PATENT DOCUMENTS

| | | |
|---|---|---|
| 6,630,507 B1 | 10/2003 | Hampson et al. |
| 2020/0009077 A1 | 1/2020 | Kennedy |
| 2020/0281890 A1 | 9/2020 | Macnair et al. |
| 2020/0289458 A1 | 9/2020 | Wong et al. |
| 2021/0093724 A1 | 4/2021 | Larosa et al. |
| 2021/0393546 A1 | 12/2021 | Crisler et al. |
| 2022/0133683 A1 | 5/2022 | Crisler |
| 2022/0347245 A1 | 11/2022 | Crisler |

FOREIGN PATENT DOCUMENTS

| | | |
|---|---|---|
| CN | 107348282 A | 11/2017 |
| EP | 1437136 B1 | 9/2005 |
| EP | 2558068 B1 | 11/2016 |
| EP | 2314284 B1 | 2/2017 |
| WO | WO2009133573 A2 | 11/2009 |
| WO | WO2012082750 A1 | 6/2012 |
| WO | WO2017011785 A1 | 1/2017 |
| WO | WO2017132526 A1 | 8/2017 |
| WO | WO2017182950 A1 | 10/2017 |
| WO | WO 2019/104442 * | 6/2019 |
| WO | WO 2019/191830 * | 10/2019 |
| WO | WO2020257588 A1 | 12/2020 |
| WO | WO2023107448 A1 | 6/2023 |
| WO | WO2023230536 A1 | 11/2023 |

* cited by examiner

*Primary Examiner* — Sahar Javanmard
(74) *Attorney, Agent, or Firm* — Alicia M. Passerin, Esq.; Leech Tishman Fuscaldo & Lampl

(57) ABSTRACT

Embodiments of the invention are directed to compositions containing cannabinoid, cannabidiol, cannabidiol isomer, or cannabidiol analog and combinations thereof for treating diabetes, and methods for treating diabetes by topically or orally administering compositions containing cannabinoid, cannabidiol, or cannabidiol analog to the patient in need of treatment.

14 Claims, 3 Drawing Sheets

COMPOSITIONS FOR PREVENTING AND TREATING DIABETES

CROSS-REFERENCE TO RELATED APPLICATIONS

This application claims priority from U.S. Provisional No. 63/049,406 entitled "Compositions for Preventing and Treating Diabetes," filed Jul. 8, 2020 the contents of which are hereby incorporated by reference in their entirety.

GOVERNMENT INTERESTS

Not applicable

PARTIES TO A JOINT RESEARCH AGREEMENT

Not applicable

INCORPORATION OF MATERIAL ON COMPACT DISC

Not applicable

BACKGROUND

The compositions and methods of embodiments can be used to treat diabetes mellitus. Diabetes mellitus ("diabetes") has two main subtypes: type 1 and type 2. Type 1 diabetes accounts for about 10% of the 200 million afflicted with diabetes and is caused by autoimmune destruction of insulin-secreting 6-cells in the pancreatic islets of Langerhans. Type 2 diabetes accounts for the remaining 90% of individuals afflicted and is often, but not always, associated with obesity. Type 2 diabetes is caused by a combination of insulin resistance and inadequate insulin secretion. Although previously termed late-onset or adult-onset diabetes, type 2 diabetes is becoming increasingly more prevalent in younger individuals.

In a non-stressed normal individual, the basal glucose level will tend to remain the same from day to day because of an intrinsic feedback loop. Any tendency for the plasma glucose concentration to increase is counterbalanced by an increase in insulin secretion and a suppression of glucagon secretion, which regulate hepatic glucose production (gluconeogenesis and release from glycogen stores) and tissue glucose uptake to keep the plasma glucose concentration constant. If the individual gains weight or becomes insulin resistant for any other reason, blood glucose levels will increase, resulting in increased insulin secretion to compensate for the insulin resistance. Therefore the glucose and insulin levels are modulated to minimize changes in these concentrations while relatively normal production and utilization of glucose are maintained.

Five different phases of insulin secretion have been identified: (1) basal insulin secretion wherein insulin is released in the postabsorptive state; (2) the cephalic phase wherein insulin secretion is triggered by the sight, smell and taste of food, before any nutrient is absorbed by the gut, mediated by pancreatic innervation; (3) early-phase insulin secretion wherein an initial burst of insulin is released within the first 5-10 minutes after the β-cell is exposed to a rapid increase in glucose, or other secretagogues; (4) second-phase insulin secretion wherein the insulin levels rise more gradually and are related to the degree and duration of the stimulus; and (5) a third-phase of insulin secretion that has only been described in vitro. During these stages, insulin is secreted, like many other hormones, in a pulsatile fashion, resulting in oscillatory concentrations in the blood. Oscillations include rapid pulses (occurring every 8-15 minutes) superimposed on slower oscillations (occurring every 80-120 minutes) that are related to fluctuations in blood glucose concentration.

In a normal individual, a meal induces the secretion of a burst of insulin, generating a relatively rapid spike in serum insulin concentration that then decays relatively quickly. This early-phase insulin response is responsible for the shut-off, or reduction, of glucose release from the liver. Homeostatic mechanisms then match insulin secretion (and serum insulin levels) to the glucose load. This is observed as a slow decay of modestly elevated serum insulin levels back to baseline and is second-phase kinetics.

Type 2 diabetics typically exhibit a delayed response to increases in blood glucose levels. While normal individuals usually begin to release insulin within 2-3 minutes following the consumption of food, type 2 diabetics may not secrete endogenous insulin until blood glucose begins to rise, and then with second-phase kinetics, that is a slow rise to an extended plateau in concentration. As a result, endogenous glucose production is not shut off and continues after consumption and the patient experiences hyperglycemia (elevated blood glucose levels). Another characteristic of type 2 diabetes is impaired insulin action, termed insulin resistance. Insulin resistance manifests itself as both a reduced maximal glucose elimination rate (GERmax) and an increased insulin concentration required to attain GERmax. Thus, to handle a given glucose load more insulin is required and that increased insulin concentration must be maintained for a longer period of time. Consequently, the diabetic patient is also exposed to elevated glucose concentrations for prolonged periods of time, which further exacerbates insulin resistance. Additionally, prolonged elevated blood glucose levels are themselves toxic to β cells.

Type 1 diabetes occurs as a result of the destruction of the insulin-producing cells of the pancreas (n-cells) by the body's own immune system. This ultimately results in a complete insulin hormone deficiency. Type 1 diabetes arises from different and less well understood circumstances. The early loss of early phase insulin release, and consequent continual glucose release, contributes to elevated glucose concentrations. High glucose levels promote insulin resistance, and insulin resistance generates prolonged elevations of serum glucose concentration. This situation can lead to a self-amplifying cycle in which ever greater concentrations of insulin are less effective at controlling blood glucose levels. Moreover, as noted above, elevated glucose levels are toxic to the p-cells, reducing the number of functional p-cells. Genetic defects impairing the growth or maintenance of the microvasculature nourishing the islets can also play a role in their deterioration. Eventually, the pancreas becomes overwhelmed, and individuals progress to develop insulin deficiency similar to people with type 1 diabetes.

SUMMARY OF THE INVENTION

Various embodiments include a composition containing a cannabinoid and, or combinations thereof, and in some embodiments, a pharmaceutical excipient, diluent, reagent, and the like and combinations thereof. In some embodiments, the cannabinoid may have a concentration of about 0.5 wt. % to about 50 wt. %, relative to the total amount of the compositions. In some embodiments, the brassinosteroid may have a concentration of about 0.01 wt. % to about 5 wt. %, relative to the total amount of the composition. In some embodiments, the composition may contain an amino acid, peptide, protein, or combination thereof, and in some embodiments, the amino acid, peptide, or protein may have a concentration of about 0.01 wt. % to about 5 wt. %, relative to the total amount of the composition. In some embodiments, the composition may further contain an antioxidant, and in some embodiments, the antioxidant may have a concentration of about 0.01 wt. % to about 5 wt. %, relative to the total amount of the topical composition. In some embodiments, the composition may include an anti-inflammatory agent, and in some embodiments, the anti-inflammatory agent may have a concentration of about 0.01 wt. % to about 5 wt. %, relative to the total amount of the topical composition. In some embodiments, the composition may include a mineral or mineral salt, and in some embodiments, the mineral or mineral salt may have a concentration of about 0.01 wt. % to about 5 wt. %, relative to the total amount of the topical composition. In some embodiments, the compositions may include cyanobacteria or green algae, and in some embodiments, the cyanobacteria or green algae may have a concentration of about 0.01 wt. % to about 5 wt. %, relative to the total amount of the topical composition. In various embodiments, the composition may be formulated as a cream, lotion, salve, liniment, ointment, gel, paste, tonic, tincture, unguent, soap, shampoo, topical, oral, pills, tablet, capsule, lip balm, or combinations thereof.

Further embodiments are directed to methods for treating diabetes mellitus by administering any of the compositions described above to a subject in need of treatment. In some embodiments, administering can be carried out by oral administration, topical administration, or combinations thereof. In some embodiments, the composition is used to treat insulin resistance and inadequate insulin secretion caused by Type 1 diabetes. In other embodiments, the composition is used to treat insulin resistance and inadequate insulin secretion caused by Type 2 diabetes. Various embodiments are directed to topical and oral formulations containing cannabinoids, cannabidiols, cannabidiol isomers, cannabidiol analogs, or combinations thereof a carrier, excipient, diluent, reagent, or combinations thereof, and an additive or combination of additives and methods for preventing and treating diabetes by topically or orally administering a composition containing cannabinoids, cannabidiols, cannabidiol isomers, cannabidiol analogs, or combinations thereof.

Some embodiments are directed to topical formulations. The formulations may include cannabidiols, cannabidiol isomers, cannabidiol analogs, or combinations thereof and a carrier, excipient, diluent, reagent, or combinations thereof. And in some embodiments, such formulations may further include one or more promoters, antibiotic agents, antioxidants, peptides, amino acid co-factors, vitamins, essential amino acids, non-essential amino acids, trace minerals, barrier agent, drying agent, hydrating agent, and combinations thereof. Such formulations may assist in blood sugar and insulin regulation.

Some embodiments are directed to oral formulations. The formulations may include cannabidiols, cannabidiol isomers, cannabidiol analogs, or combinations thereof and a carrier, excipient, diluent, reagent, or combinations thereof. And in some embodiments, such formulations may further include one or more brassinosteroid agents, antibiotic agents, antioxidants, peptides, amino acid co-factors, vitamins, essential amino acids, non-essential amino acids, trace minerals, barrier agent, drying agent, hydrating agent, and combinations thereof. Such formulations may assist in blood sugar and insulin regulation.

DESCRIPTION OF THE DRAWINGS

Examples of the specific embodiments are illustrated in the accompanying drawings. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention. In the following description, numerous specific details are set forth in order to provide a thorough understanding of the present invention. The present invention may be practiced without some or all of these specific details. In other instances, well known process operations have not been described in details so as to not unnecessarily obscure the present invention.

The patent or application file contains at least one drawing executed in color. Copies of this patent or patent application publication with color drawing(s) will be provided by the office upon request and payment of the necessary fee.

DETAILED DESCRIPTION

Figure 1A:
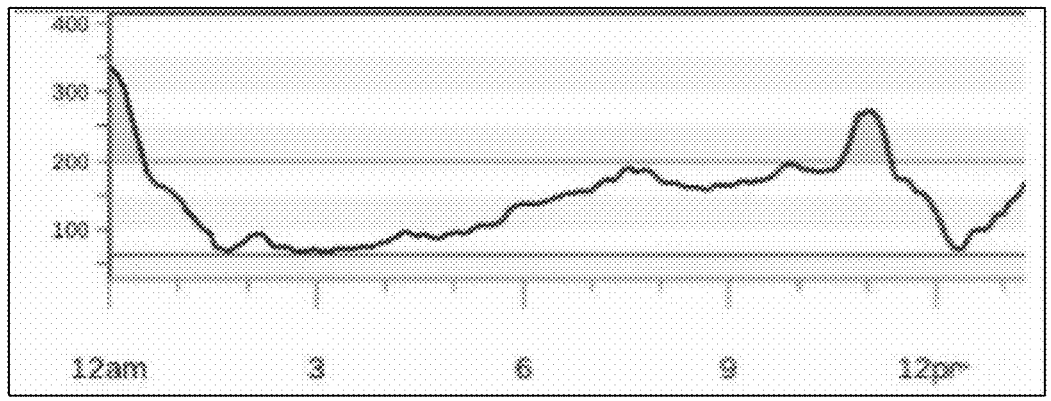
FIG. 1A is a chart showing glucose levels of a diabetic patient before administration of the compositions of the invention.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 ml to 8 ml is stated, 2 ml, 3 ml, 4 ml, 5 ml, 6 ml, and 7 ml are also intended to be explicitly disclosed, as well as the range of values greater than or equal to 1 ml and the range of values less than or equal to 8 ml.

All percentages, parts and ratios are based upon the total weight of the topical compositions and all measurements made are at about 25° C., unless otherwise specified.

The singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

The word "about" when immediately preceding a numerical value means a range of plus or minus 10% of that value, e.g, "about 50" means 45 to 55, "about 25,000" means 22,500 to 27,500, etc, unless the context of the disclosure indicates otherwise, or is inconsistent with such an interpretation. For example, in a list of numerical values such as about 49, about 50, about 55, "about 50" means a range extending to less than half the interval(s) between the preceding and subsequent values, e.g, more than 49.5 to less than 52.5. Furthermore, the phrases "less than about" a value or "greater than about" a value should be understood in view of the definition of the term "about" provided herein.

The terms "administer," "administering" or "administration" as used herein refer to either directly administering a compound (also referred to as an agent of interest) or pharmaceutically acceptable salt of the compound (agent of interest) or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical, cosmetic or other agent across a tissue layer such as the stratum corneum or stratum spinosum.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. In embodiments or claims where the term comprising is used as the transition phrase, such embodiments can also be envisioned with replacement of the term "comprising" with the terms "consisting of" or "consisting essentially of."

The term "disorder" is used in this disclosure to mean, and is used interchangeably with the terms disease, condition, symptom, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject or enhance the texture, appearance, color, sensation, or hydration of the intended tissue treatment area. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The phrase "pharmaceutically acceptable" or "cosmetically acceptable" is employed herein to refer to those agents of interest/compounds, salts, compositions, dosage forms, etc, which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, pharmaceutically acceptable means approved by a regulatory agency of the federal or state government, or listed in the U.S. Pharmacopeia or other generally recognized pharmacopeia for use in mammals (e.g, animals), and more particularly, in humans.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Non-limiting examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, aryl aliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid.

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

The term "treating" is used herein, for instance, in reference to methods of treating a skin disorder or a systemic condition, and generally includes the administration of a compound or composition which reduces the frequency of, or delays the onset of, symptoms of a medical condition or enhance the texture, appearance, color, sensation, or hydration of the intended tissue treatment area of the tissue surface in a subject relative to a subject not receiving the compound or composition. This can include reversing, reducing, or arresting the symptoms, clinical signs, and underlying pathology of a condition in a manner to improve or stabilize a subject's condition.

The term "herb" is used herein, for instance, in reference to plants that in certain embodiments and delivered by appropriate methods have a therapeutic or medicinal purpose, such as, but not limited to river mint, eucalyptus, wattle, cocoa, plants of the family cannabaceae, plants containing cannabinoids, and plants containing cannabinoid precursors and analogs.

The terms "cannabinoid," "cannabidiol," "CBD," "cannabidiolic acid," "CBDA," and other compound names and abbreviations are meant to describe the compound itself or a class of compounds having similar structural characteristics. Such terms are not used to describe combinations of such compounds as found, for example, in hemp seed oil or other extracts that are known and understood to contain a variety of compounds other than, for example, cannabidiol, in unknown concentrations. The reader should assume, unless otherwise indicated, that the terms "cannabidiol," "CBD," "cannabidiolic acid," "CBDA," or "analogs of cannabidiol" as used herein refer to preparations of cannabidiol, cannabidiolic acid, or analogs of cannabidiol that are nearly 100% pure cannabidiol, cannabidiolic acid, or an analog of cannabidiol and devoid of any measurable quantity of other compounds found in extracts.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason. Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Various embodiments are directed to compositions for treating diabetes containing cannabinoids and methods for using such compositions to treat, prevent, and ameliorate diabetes and the symptoms related thereto. The methods for treating diabetes of some embodiments may include the step of administering such compositions to a person in need of treatment, having type 1 or type 2 diabetes. Such compositions may be administered in therapeutically effective doses orally or topically. The compositions and methods of the invention may improve the glucose uptake and level blood glucose levels and reduce the need for or frequency of insulin administration to produce stable blood glucose levels. The compositions may further reduce A1c levels, the percentage of sugar in the blood attached to hemoglobin, in diabetic patients. In some embodiments, the compositions and methods of the invention may enhance the effectiveness of insulin therapy, improving the stability of blood glucose levels over a longer period of time than insulin therapy alone.

The compositions and methods of embodiments can be used to treat diabetes mellitus. Diabetes mellitus ("diabetes") has two main subtypes: type 1 and type 2. Type 1 diabetes accounts for about 10% of the 200 million afflicted with diabetes and is caused by autoimmune destruction of insulin-secreting 6-cells in the pancreatic islets of Langerhans. Type 2 diabetes accounts for the remaining 90% of individuals afflicted and is often, but not always, associated with obesity. Type 2 diabetes is caused by a combination of insulin resistance and inadequate insulin secretion. Although previously termed late-onset or adult-onset diabetes, type 2 diabetes is becoming increasingly more prevalent in younger individuals.

The cannabinoids of of various embodiments include any of a broad class of compounds that are known to interact with cannabinoid receptors, and encompass endocannabinoids (produced naturally in the body by animals), the phytocannabinoids (found in cannabis and some other plants), and synthetic cannabinoids (manufactured artificially). Example cannabinoids include, but are not limited to, tetrahydropyran analogs, such as, $\Delta^9$-tetrahydrocannabinol, tetrahydrocannabinol, $\Delta^8$-tetrahydrocannabinol, 6,6,9-trimythel-3-pentyl-6H-dibenzo[b,d]pyran-1-ol, 3-(1,1-dimethylheptyl)-6,6a7,8,10,10a-hexahydro-1-1hydroxy-6,6-dimythel-9H-dibezo[b,d]pyran-9-ol, (−)-(3S,4S)-7-hydroxy-delta-6-tetrahydrocannabino1-1,1-dimethylheptyl, (+)-(3S,4S)-7-hydroxy-Δ-6-tetrahydrocannabinol, and $\Delta^8$-tetrahydrocannabinol-11-oic acid, piperidine analogs, such as, (−)-(6S,6aR,9R,10aR)-5,6,6a,7,8,9,10,10a-octahydro-6-methyl-1-3-[(R)-1-methyl-4-phenylbutoxy]-1,9 phenanthridinediol 1-acetate), aminoalkylindole analogs, such as, (R)-(+)-[2,3-dihydro-5-methyl-3-(4-morpholinylmethyl)-pyrrolo[1,2,3,-de]-1,4-benzoxazin-6-yl]-1-naphthelenyl-methanone, open pyran-ring analogs, such as, 2-[3-methyl-6-(1-methylethenyl-2-cyclohexen-1-yl]-5-pentyl-1, 3-benzendi-ol, and 4-(1,1-dimethylheptyl)-2,3'-dihydroxy-6'-α-(3-hydroxypropyl)-1',-2',3',4',5 ', 6'-hexahydrobiphenyl, lipophilic alkylamides, such as, dodeca-2E, 4E, 8Z, 10E/Z-tetraenoic-acid-isobutylamide, cannabinoid mimetics, salts, solvates, metabolites, and metabolic precursors of these compounds and combinations thereof. In some embodiments, cannabinoids may be derived plants including hemp, *Echinacea purpurea, Echinacea angustifolia, Acmella oleracea, Helichrysum umbraculigerum, Radula marginata*, and combinations thereof and oils made from these plants, and in other embodiments, cannabinoids may be manufactured or chemically synthesized.

The compositions of various embodiments can include any number of cannabinoids in various concentrations; however, in certain embodiments, the cannabinoid may be cannabidiol (2-(6-isopropenyl-3-methyl-5-cyclohexen-1-yl)-5-pentyl-1,3-benzenediol). Cannabidiol has 7 double bonds and 30 stereoisomers. Embodiments include compositions containing each stereoisomer individually and compositions containing a combination of these stereoisomers. In particular embodiments, the compositions used in the methods of embodiments and the compositions of embodiments may include high concentrations of cannabidiol. For example, in some embodiments, cannabidiol may be about 30 w/v % to about 100 w/v % of the cannabinoids in the composition, and in other embodiments cannabidiol may be about 50 w/v % to about 100 w/v %, about 75 w/v % to about 100 w/v %, about 80 w/v % to about 100 w/v %, about 90 w/v % to about 100 w/v % of the cannabinoids in the composition.

Cannabidiol can be obtained by cold-pressing industrial hemp with trace amounts of THC. Cannabidiol in this present invention is provided as a natural constituent of hemp oil.

In some embodiments, the cannabinoids in the composition may be cannabidiol analogs. The term "cannabidiol analogs" refers to synthetically produced compounds that are structurally similar, but not structurally identical, to cannabidiol. Various cannabidiol analogs are known in the art and embodiments encompass such cannabidiol analogs. For example, PCT Publication WO2017/132526 and U.S. Pat. No. 6,630,507, which are each hereby incorporated by reference in their entireties, describes various analogs of cannabidiol. In some embodiments, the analogs of cannabidiol may be of general Formula I:

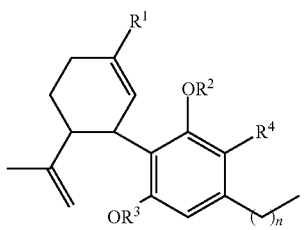

where $R^1$ is hydrogen, methyl, linear or branched $C_2$-$C_{10}$ alkyl, linear or branched $C_2$-$C_{10}$ alkenyl, linear or branched $C_2$-$C_{10}$ substituted alkyl, linear or branched $C_2$-$C_{10}$ substituted alkenyl, $R^2$ and $R^3$ are each, individually, hydrogen, methyl, linear or branched $C_2$-$C_{10}$ alkyl, linear or branched $C_2$-$C_{10}$ substituted alkyl, linear or branched $C_2$-$C_{10}$ alkenyl, linear or branched $C_2$-$C_{10}$ substituted alkenyl, linear or branched $C_2$-$C_{10}$ acyl, linear or branched $C_2$-$C_{10}$ substituted acyl, an amine or amino acid, amino acid ester, $R^4$ is hydrogen, substituted or unsubstituted alkyl, carboxyl, alkoxy, aryl, aryloxy, arylalkyl, halo or amino, and n may an integer of 2 to 10 and the like and salts and solvates thereof. In some embodiments, $R^2$ and $R^3$ may, independently, be a linear or branched, substituted or unsubstituted $C_2$-$C_{10}$ acyl having a carboxylic acid terminus thereby producing a dicarboxylic acid, and salts thereof. Like cannabidiol, cannabidiol analogs can have various isomers. Embodiments include all isomers of the such cannabidiol analogs.

In some embodiments, cannabidiol analogs, such as those described above may be combined with cannabidiol, to produce a mixture of cannabidiol and cannabidiol analogs. Thus, as used herein the term "cannabidiol" encompasses cannabidiol, cannabidiol analogs, and the various isomers of cannabidiol and cannabidiol analogs.

The compositions of various embodiments can include up to about 50% (w/w) cannabidiol, cannabidiol analogs, isomers of cannabidiol, cannabidiol analogs, and combinations thereof (collectively, "cannabidiol"), and in some embodiments, the compositions may include from about 50% (w/w) to about 0.5% (w/w), about 30% (w/w) to about 1% (w/w), about 20% (w/w) to about 1% (w/w), about 20% (w/w) to about 5% (w/w) cannabidiol, or any range of or individual concentration encompassed by these example ranges. In particular embodiments, the composition may include about 15% (w/w) to about 10% (w/w) cannabidiol.

In certain embodiments, the cannabidiol of embodiments described above may be cannabidiolic acid ("CBDA"). Without wishing to be bound by theory, CBDA may exhibit improved hydrophilicity over other isomers of cannabidiol, which may allow for improved solubility and delivery of CBDA to the skin. The CBDA may be modified, partially digested, or otherwise acted upon by enzymes in the skin to produce for example cannabidiol (CBD), which may be the active form cannabidiol in the composition. Thus, CBDA may act as a prodrug in some embodiments of the invention. Other cannabidiol analogs or isomers may produce a similar effect and are encompassed by prodrug embodiments of the invention.

The cannabidiol in the compositions of embodiments of the invention may be 100% cannabidiol, or oils, solvents, and emulsions containing cannabidiol. For example, in some embodiments, the compositions of the invention may include cannabidiol derived from hempseed oil. Hempseed oil is generally manufactured from varieties of Cannabis sativa that do not contain significant amounts of tetrahydrocannabinol (THC), the psychoactive element present in the cannabis plant. This manufacturing process typically includes cleaning the seed to 99.99% before pressing the oil. Hempseed oil generally also contains omega-6 and omega-3 fatty acids. For example, about 30-35% of the weight of hempseed oil are essential fatty acids (EFAs), i.e., linoleic acid, omega-6 (LA, 55%), α-linolenic acid, omega-3 (ALA, 22%), γ-linolenic acid, omega-6 (GLA, 1-4%),and stearidonic acid, omega-3 (SDA, 0-2%). Thus, the compositions of some embodiments may contain fatty acids such as omega-6 and omega-3 fatty acids.

Oils include cannabidiol oil and various plant derived oils containing cannabidiol such as hempseed oil, *Echinacea purpurea*, *Echinacea angustifolia*, *Acmella oleracea*, *Helichrysum umbraculigerum*, *Radula marginata*, and the like. In some embodiments, cannabidiol isolated from such plants or made synthetically may be formulated with an oil such as, for example, olive oil, grapeseed oil, tea tree oil, almond oil, avocado oil, sesame oil, evening primrose oil, sunflower oil, kukui nut oil, jojoba oil, walnut oil, peanut oil, pecan oil, macadamia nut oil, coconut oil, and the like and combinations thereof.

Unless indicated otherwise, the term "therapeutically effective amount" is not particularly limited, so long as the cannabinoid is present in an amount effective for treating the dermatological disease. The therapeutically effective amount of cannabinoid can be from about 2 milligrams per kilogram (mg/kg) to about100 mg/kg, about 2 mg/kg to about 50 mg/kg, about 2 mg/kg to about 25 mg/kg, or any range or individual concentration encompassed by these example ranges, wherein mg refers to the mass or weight of the cannabinoids and kg refers to the mass or weight of the patient in need of treatment. In certain embodiments, a therapeutically effective amount of CBD in the composition may be about 2 mg/kg to about 10 mg/kg or any range or individual concentration encompassed by these example ranges, wherein mg refers to the mass or weight of the cannabinoids and kg refers to the mass or weight of the patient in need of treatment. In certain embodiments, a therapeutically effective amount of CBD is from about 2 mg/kg to about 100 mg/kg, about 2 mg/kg to about 50 mg/kg, and about 2 mg/kg to about 25 mg/kg, or about 2 mg/kg to about 10 mg/kg. All rational numbers between the preceding minima and maxima are included in the ranges.

In some embodiments, the compositions may further include a promoter such as vinca alkaloids, fatty acids, triazoles, taxoi and derivatives thereof, pyrrolidones, piperazines, piperidines, pyridines, pryidones, pyrrolidines, retinoids, salicylates, sorbitans, phenothiazines, polyethylene glycols, colchicine, cephalosporins, cyclic peptides, flavones, flavonoids, opioids, phenylalkylamines, amino acridines, aminoquinolines, anilides, anthracyclines, antibiotics, antiestrogens, imidazoles, (iso)quinolines, benzofurans, benzodiazepines, benzhydryl compounds, benzazepines, dibenzazepines, epipodophyllotoxins, macrolides, rauwolfia alkaloids, and steroids. In further embodiments, the selected promoter is a flavonoid, and in certain embodiments, the flavonoid is quercetin.

The amount of promoter is not limited and includes any therapeutically effective amount. For example, in some embodiments, the amount of promoter may be about 0.01 wt. % to about 5 wt %, relative to the total amount of the composition, about 0.1 wt. % to about 1 wt %, relative to the total amount of the formulation, or any range or individual concentration encompassed by these example ranges.

In some embodiments, the compositions may further include an anti-inflammatory compound such as hyaluronic acid, curcumin, glutathione, methotrexate, tofacitinib, 6-mercaptopurine, azathioprine sulphasalazine, mesalazine, olsalazine chloroquinine/hydroxychloroquinine, penicillamine, aurothiomalate (intramuscular and oral), azathioprine, cochicine, corticosteroids (oral, inhaled, and local injection), a beta-2 adrenoreceptor agonist (salbutamol, terbutaline, salmeteral), a xanthine (theophylline, aminophylline), cromoglycate, nedocromil, ketotifen, ipratropium and oxitropium, cyclosporin, FK506, rapamycin, mycophenolate mofetil, leflunomide, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) and p55TNFRigG (Lenercept), siL-1RI, siL-1RII, siL-6R), an antiinflammatory cytokine (e.g. IL-4, IL-1 0, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCV acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL1S, BIRB-796, SCI0-469, VX-702, AMG-548, VX-740, Roflumilast, IC-485, CDC-801, S1PI agonists (such as FTY720), a PKC family inhibitor (e.g. Ruboxistaurin or AEB-071) or Mesopram, budenoside; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, IL-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid (e.g. prednisolone); a phosphodiesterase inhibitor; an adenosine agonist; an antithrombotic agent; a complement inhibitor; an adrenergic agent; an agent that interferes with signalling by proinflammatory cytokines such as TNF or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-1RI, siL-1RII, siL-6R), an antiinflammatory cytokine (e.g. IL-4, IL-1 0, IL-11, IL-13 or TGF), therapeutic agents that target an intrinsic checkpoint blockade, such as, for example, the gene encoding Cytokine-inducible $SH_2$-containing protein (CISH), antibody BGB-A317, Nivolumab, or Pembrolizumab, atezolizumab, avelumab, durvalumab, ipilimumab, and the like and combinations thereof.

The amount of anti-inflammatory agent is not limited and includes any therapeutically effective amount. For example, in some embodiments, the amount of anti-inflammatory agent may be about 0.01 wt. % to about 5 wt %, relative to the total amount of the composition, about 0.1 wt. % to about 1 wt %, relative to the total amount of the formulation, or any range or individual concentration encompassed by these example ranges.

In some embodiments, the compositions may include an antioxidant. Such antioxidant may be, for example, butylated hydroxytoluene, ascorbic acid, ascorbyl palmitate, butylated hydroxyanisole, 2,4,5-trihydroxy butyrophenone, 4-hydroxymethyl-2,6-di-tert-butylphenol, erythorbic acid, gum guaiac, propyl gallate, thiodipropionic acid, dilauryl thiodipropionate, tert-butylhydroquinone, tocopherol, glutathione, and the like and pharmaceutically acceptable salt or ester thereof or combinations thereof. The antioxidant can be present in a concentration of about 0.01% (w/w) to about 1% (w/w) of the total composition or any individual concentration encompassed by this example range.

In certain embodiments, the composition may include a combination of a flavonoid and an antioxidant. For example, in some embodiments, the composition may include a combination of quercetin and ascorbyl palmitate. Without wishing to be bound by theory, the composition of a flavonoid, such as quercetin, and an antioxidant, such as ascorbyl palmitate, may improve the availability of the cannabinoid in the composition, improving efficacy by up to about 10%, about 2% and about 5%, or any range or individual improvement encompassed by these ranges.

In some embodiments, the compositions may further include an antibiotic. The type of antibiotic is not limited, and can be, for example, subtilosin, ampicillin, bacampicillin, carbenicillin indanyl, mezlocillin, piperacillin, ticarcillin, amoxicillin-clavulanic acid, ampicillin-sulbactam, benzylpenicillin, cloxacillin, dicloxacillin, methicillin, oxacillin, penicillin G, penicillin V, piperacillin tazobactam, ticarcillin clavulanic acid, nafcillin, procaine penicillin, cefadroxil, cefazolin, cephalexin, cephalothin, cephapirin, cephradine, cefaclor, cefamandol, cefonicid, cefotetan, cefoxitin, cefprozil, cefmetazole, cefuroxime, loracarbef cefdinir, ceftibuten, cefoperazone, cefixime, cefotaxime, cefpodoxime proxetil, ceftazidime, ceftizoxime, ceftriaxone, cefepime, azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, perfloxacin, imipenem-cilastatin, meropenem, and aztreonam.

The amount of the antibiotic in the compositions is not limited, and includes any therapeutically effective amount. For example, the antibiotic may have a concentration of about 0.01 wt. % to about 5 wt %, relative to the total amount of the composition, about 0.1 wt. % to about 1 wt %, relative to the total amount of the composition, or any range or individual concentration encompassed by these example ranges.

In some embodiments, the composition may further include a plant extract such as, but not limited to, phytochemicals. Phytochemicals can include chemical compounds that naturally occur in plants such as flavonoids or bioflavonoids. Bioflavonoids can include flavonoids, isoflavanoids, neoflavanoids, and anthoxanthins flavones (e.g., luteolin, apigenin, and tangeritin), flavonols (e.g., quercetin, kaempferol, myricetin, fisetin, galangin, isorhamnetin, pachypodol, rhamnazin, pyranoflavonols, and furanoflavonols), flavones (e.g., hesperetin, naringenin, eriodictyol, and homoeriodictyol), flavanonol (e.g., taxifolin and dihydrokamferol), flavans (e.g., flavan-3-ols, anthocyanidins, and isoflavinoids). In other embodiments, upregulating compounds comprise extracts derived from edible plants. For example, the plant extracts may include glucoraphnin or sulforaphanederived derived from broccoli, catechin, epicatachin, and proanthocyanidins from grapes, grape seed extract, milk thistle, and blueberries, and other related compounds. In certain embodiments, the plant extract may include alpha lipoic acid, resveratrol, curcumin, EGCG, Olivol®, rutin, quercetin, hesperetin, and the like and combinations thereof.

In some embodiments of the present invention, compositions may further contain a mineral, mineral salt, or combinations thereof. Such minerals are not limited, and can include selenium, sulfur, zinc, iron, chlorine, cobalt, copper, manganese, molybdenum, and iodine.

The amount of the mineral or mineral salts in the topical formulation is not limited, and includes any therapeutically effective amount. For example, the mineral or mineral salt may have a concentration of about 0.01 wt. % to about 5 wt %, relative to the total amount of the composition, about 0.1 wt. % to about 1 wt %, relative to the total amount of the composition, or any range or individual concentration encompassed by these example ranges.

In some embodiments of the present invention, the compositions may further include a vitamin or a combination of vitamins. Vitamins are organic molecules that are essential nutrients that organisms need to sustain proper biological function and metabolism. The vitamins encompassed by the invention are not limited, and can be, for example, vitamin A, vitamin $B_1$, vitamin $B_2$, vitamin $B_3$, vitamin $B_4$, vitamin $B_5$, vitamin $B_6$, vitamin $B_7$, vitamin $B_8$, vitamin $B_9$, vitamin $B_{10}$, vitamin $B_{11}$, vitamin $B_{12}$, vitamin C, vitamin D, vitamin E, and vitamin K.

The amount of the vitamin in the topical formulation is not limited, and can be any therapeutically effective amount. For example, the vitamin may have a concentration of about 0.01 wt. % to about 5 wt %, relative to the total amount of the composition, about 0.1 wt. % to about 1 wt %, relative to the total amount of the composition, or any range or individual concentration encompassed by these example ranges.

In some embodiments, the compositions may further contain amino acids, peptides, or combinations thereof. Amino acids are organic compounds that combine through peptide bond formation to form peptides and proteins. Amino acids can chemically combine through peptide bond formation to form dipeptides, tripeptides, tetrapeptides, oligopeptides, polypeptides, peptides, and proteins. Amino acids are the building blocks for living organisms. The human body uses amino acids to break down food, grow, repair body tissue, and perform other necessary biological processes. The amino acid is not limited, and can be at least one member selected from the group consisting of L-arginine, D-arginine, L-histidine, D-histidine, L-lysine, D-lysine, L-aspartic acid, D-aspartic acid, L-glutamic acid, D-glutamic acid, D-serine, L-serine, L-threonine, D-threonine, D-asparagine, L-asparagine, L-glutamine, D-glutamine, L-cystine, D-cysteine, L-selenocysteine, D-selenocysteine, L-glycine, D-glycine, L-proline, D-proline, L-alanine, D-alanine, L-valine, D-valine, L-isoleucine, D-isoleucine, L-leucine, D-leucine, L-methionine, D-methionine, L-phenylalanine, D-phenylalanine, L-tyrosine, D-tyrosine, L-tryptophan, D-tryptophan, and the like and combinations thereof.

The amount of the amino acids, peptides, or combinations thereof in the composition is not limited, and includes any therapeutically effective amount. For example, the amino acid, peptides, or combinations thereof may have a concentration of about 0.01 wt. % to about 5 wt %, relative to the total amount of the composition, about 0.1 wt. % to about 1 wt %, relative to the total amount of the composition, or any range or individual concentration encompassed by these example ranges.

In some embodiments, the compositions may further include cyanobacteria, green algae, or combinations thereof, such as, aphanizomenon flos-aquae (E3Live™), Arthrospira platensis, Synechocystis, Spirulina, photoautotrophic cyanobacteria, and combinations thereof. Cyanobacteria are a phylum of bacteria that include photosynthetic prokaryotes able to produce oxygen. Cyanobacteria may possess the ability to produce substances that serve as anti-inflammatory agents and combat infection in humans. Some cyanobacteria have been shown to trigger substantial movement of natural killer cells (NKCs), which are cells that provide rapid response to virus-infected cells.

The amount of cyanobacteria, green algae, or combinations thereof in the compositions is not limited, and includes any therapeutically effective amount. For example, cyanobacteria, green algae, or combinations thereof in the compositions may have a concentration of about 0.01 wt. % to about 5 wt %, relative to the total amount of the composition, about 0.1 wt. % to about 1 wt %, relative to the total amount of the composition, or any range or individual concentration encompassed by these example ranges.

In some embodiments, the compositions of the invention may be formulated as a topical composition. As such, the compositions may be formulated as creams, liniments, ointments, lotions, and the like. In other embodiments, the compositions of the invention may be formulated for oral administration. The compositions may be formulated as tinctures, tonics, tablets, capsules, and the like.

Creams refer to semi-solid emulsions of oil and water in approximately equal proportions. They are divided into two types: oil-in-water (01W) creams, composed of small droplets of oil dispersed in a continuous phase; and water-in-oil (W/O) creams, composed of small droplets of water dispersed in a continuous oily phase. Creams can provide a barrier to protect the skin. This may be a physical barrier or a chemical barrier as with UV-absorbing compounds. To aid in the retention of moisture (especially water-in-oil creams), creams are usually used for a variety of purposes including cleansing, emollient effects, and as a vehicle for drug substances such as local anesthetics, anti-inflammatories (NSAIDs or corticosteroids), hormones, antibiotics, antifungals or counter-irritants.

Liniments or balms are topical formulations that are of a similar viscosity to lotions and less viscous than an ointment or cream. Liniments are generally applied with friction by rubbing the liniment into the skin. Liniments typically are formulated from alcohol, acetone, or similar quickly evaporating solvents and may contain counterirritant aromatic chemical compounds such as methyl salicylate, benzoin resin, or capsaicin.

Ointments are compositions in which oil and water are provided in a ratio of from 7:1 to 2:1, from 5:1 to 3:1, or 4:1. Ointments are generally formulated using oils, waxes, water, alcohols, petroleum products, water, and other agents to prepare formulations with various viscosities and solvent properties. Commonly used formulations include oleaginous base (White Ointment), absorption base, W/O emulsion base (Cold Cream type base), O/W emulsion base (Hydrophilic Ointment), water soluble base, in addition to others. These preparations are used to dissolve or suspend substances or products with medicinal or cosmetic value.

Lotions are low-to medium-viscosity topical preparation. Most lotions are oil-in-water emulsions containing an emulsifier such as cetyl alcohol to prevent separation of these two phases. Lotions can include fragrances, glycerol, petroleum jelly, dyes, preservatives, proteins and stabilizing agents.

In some embodiments, the composition can be in the form of a tincture. Tinctures are herbal extracts that provide a method for oral administration of an herbal component or components to a subject in need of treatment. Tinctures are prepared by mixing an herb or herbs or components and combinations thereof with a suitable solvent wherein a component or components of an herb or herbs or combinations thereof are extracted into a solvent in which the component or components of the herb are reasonably soluble. Suitable tincture solvents in the present invention include pharmacologically acceptable solvents such as organic solvents, water based solvents, alcohols, and other orally administrable solvents such as, but not limited to, water, purified water, preserved water, vegetable glycerin, propylene carbonate, 3-methoxy-3-methyl-1-butanol (MMB), polyethylene glycol, glycerol, rice bran oil, and combinations thereof. Tinctures may be administered orally by swallowing the tincture or sublingually, by administering the tincture below the tongue, where the active ingredients are absorbed into the bloodstream. In certain embodiments, administration may be carried out sublingually.

In some embodiments, the composition can be in the form of a tonic. Tonics are extracts that provide a method for oral administration of an herbal component or components to a subject in need of treatment. Tonics are prepared by mixing an herb or herbs or components and combinations thereof with a suitable solvent wherein a component or components of an herb or herbs or combinations thereof are extracted into a solvent by aid of heating, often heat necessary such that the solvent reaches its boiling temperature, in which the component or components of the herb are reasonably soluble. Suitable tonic solvents in the present invention include pharmacologically acceptable solvents such as organic solvents, water based solvents, alcohols, and other orally administrable solvents such as, but not limited to, water, purified water, preserved water, vegetable glycerin, propylene carbonate, 3-methoxy-3-methyl-1-butanol (MMB), polyethylene glycol, glycerol, rice bran oil, and combinations thereof.

In some embodiments, the composition can be in the form of a tablet. Tablets are pharmaceutical oral dosage forms of a medicament or medicaments that are formed by molding or compression. Such embodiments of the medicament or medicaments and may further include suitable excipients such as, but not limited to, diluents, binders, granulating agents, glidants, lubricants, disintegrants, sweeteners, and pigments. Tablets in the present invention may also be coated with a pigment to increase the visual appearance of the tablet, to increase the identifiability of the tablet, to increase the ease with which the tablet is orally administered, to make the tablet more easily swallowed, to control the release of the medicament or medicaments, or to make the tablet more resistant to environmental degradation factors, or a combination or combinations thereof.

In some embodiments, the composition can be in the form of a capsule. Capsules generally fall within the class of either hard-shelled capsules or soft-shelled capsules, but need not be restricted to either class. Hard shelled capsules generally, but need not necessarily, contain dry, powdered, or granular components while soft-shelled capsules primarily, but need not necessarily, contain oils or medicaments or combinations thereof.

Various embodiments are directed methods for treating diabetes by administering any of the compositions described above including cannabinoid to the subject in need of treatment. Administering can be carried out topically, orally, or in combination thereof. For example, in some embodiments, the method may include applying a therapeutically effective amount of a topical composition containing cannabinoid to the skin of a patient having type 1 or type 2 diabetes. In some embodiments, administering can be carried out 2 to 6 times per day, and in some embodiments, administering can be carried out after a change in blood glucose level. In other embodiments, the method may include orally administering a therapeutically effective amount of an oral composition containing cannabinoid to a patient having type 1 or type 2 diabetes. In some embodiments, administering can be carried out 2 to 6 times per day, and in some embodiments, administering can be carried out after a change in blood glucose level.

In some embodiments, the methods described above, both topical and oral administration, may further include the step of administering insulin to the patient having type 1 or type 2 diabetes. Insulin can be administered by any means including oral and by injection, particularly, subcutaneous injection. Notably, in some embodiments, administration of insulin is not necessary to reduce or completely mitigate the effects of diabetes and improve the overall health of diabetic patients under treatment.

Additional embodiments of the invention include methods of making the topical formulation in the form of a cream, which comprises (i) dispersing lake/powder into mineral oil or silicone oil to obtain an oil phase; (ii) dispersing an emulsifier, a thickener; and a stabilizer into water in a separate vessel to obtain an aqueous phase; (iii) blending the oil phase and the aqueous phase to form an emulsion; and (iv) dispersing an active ingredient such as a Cannabis derived botanical drug product into at least one of the oil phase, the aqueous phase, and the emulsion. In some embodiments, the method further comprises heating during at least one of (i) dispersing lake/powder into mineral oil or silicone oil to obtain an oil phase and (ii) dispersing an emulsifier, a thickener; and a stabilizer into water in a separate vessel to obtain an aqueous phase. Temperatures of this heating are not particularly limited, so long as the oil phase and the aqueous phase result from the dispersing.

In some embodiments, topical formulations in the form of a lotion can be made by mixing an oil phase comprising hemp oil with an emulsifier and with an aqueous phase to form a mixture and heating said mixture at a temperature of from 45 and 85° C. to form an aqueous emulsion. Emulsifiers include, but are not limited to, cetyl alcohol, stearic acid, and a mixture thereof. The water phase comprises a stabilizing agent such as VEEGUM® or CARBOPOL®.

Tables 1-2 below provide specific examples of formulations encompassed by the invention. The compositions of Table 1 includes hyaluronic acid, which is an optional ingredient, but may be beneficial in certain applications.

TABLE 1

| | |
|---|---|
| CBD or analog or combinations thereof | 2 to 100 milligrams |
| Hyaluronic acid | 0.5-1.5% (w/w) |
| Quercetin | 0.01-5% (w/w) |
| Glutathione | 800-1500 mg |
| Vitamin C | 350-1000 mg |
| L-lysine | 1000-3000 mg |
| Selenium | 55-125 mg |
| Sulfur | 1000-1500 mg |
| Zinc | 10-15 mg |

The compositions of Table 2 does not include hyaluronic acid, but is effective for treating diabetes.

TABLE 2

| | |
|---|---|
| CBD or analog or combinations thereof | 2 to 100 milligrams |
| Quercetin | 0.01-5% (w/w) |
| Glutathione | 800-1500 mg |
| Vitamin C | 350-1000 mg |
| L-lysine | 1000-3000 mg |
| Selenium | 55-125 mg |
| Sulfur | 1000-1500 mg |
| Zinc | 10-15 mg |

Another embodiment of the present invention is a method of making the topical formulation in the form of a cream, which comprises (i) dispersing lake/powder into mineral oil or silicone oil to obtain an oil phase; (ii) dispersing an emulsifier, a thickener; and a stabilizer into water in a separate vessel to obtain an aqueous phase; (iii) blending the oil phase and the aqueous phase to form an emulsion; and (iv) dispersing an active ingredient such as a Cannabis derived botanical drug product into at least one of the oil phase, the aqueous phase, and the emulsion. In some embodiments, the method further comprises heating during at least one of (i) dispersing lake/powder into mineral oil or silicone oil to obtain an oil phase and (ii) dispersing an emulsifier, a thickener; and a stabilizer into water in a separate vessel to obtain an aqueous phase. Temperatures of this heating are not particularly limited, so long as the oil phase and the aqueous phase result from the dispersing.

Another embodiment of the present invention is a method of making the topical formulation in the form of a lotion, which comprises mixing an oil phase comprising hemp oil with an emulsifier and with an aqueous phase to form a mixture and heating said mixture at a temperature of from 45 and 85° C. to form an aqueous emulsion. Emulsifiers include, but are not limited to, cetyl alcohol, stearic acid, and a mixture thereof. The water phase comprises a stabilizing agent such as VEEGUM® or CARBOPOL®.

Another embodiment of the present invention is a method of making the topical formulation in the form of a shampoo, which comprises combining a surfactant, most often sodium lauryl sulfate and/or sodium laureth sulfate with a co-surfactant, most often cocamidopropyl betaine, in an aqueous phase and mixing the aqueous phase to form a thick, viscous liquid. Preferred methods further comprise adding other ingredients, such as salt (sodium chloride), a preservative, and fragrance, to the aqueous phase.

Unless indicated otherwise, the term "therapeutically effective amount" is not particularly limited, so long as at least one of THC and CBD is present in an amount effective for treating the dermatological disease. Preferably, the therapeutically effective amount of at least one of THC and CBD is from 2 to 100 milligrams per kilogram, more preferably from 2 to 50 milligrams per kilogram, and more preferably from 2 to 25 milligrams per kilogram. The most preferred therapeutically effective amount of THC and/or CBD in the topical formulation according to the present invention is from 2 to 10 milligrams per kilogram. All rational numbers between the preceding minima and maxima are included in the ranges.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

A diabetes patient was administered the oral composition during a normal course of treatment. Blood sugar levels were recorded every 5 minutes 24 hours a day. Random spikes in blood sugar are normal but were greatly reduced during the course of treatment. When the patient temporarily paused taking the composition for 5 days, unpredictable, random spiking in blood sugar occurred as it had before the start of treatment.

Figure 1B:
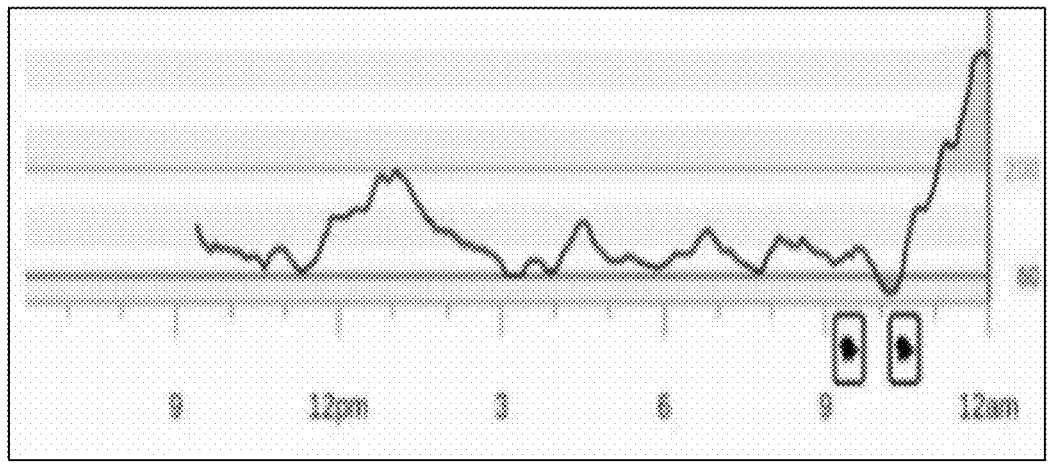
FIG. 1B is a chart showing glucose levels of a diabetic patient before administration of the compositions of the invention.

FIG. 1A and FIG. 1B show the patient's blood sugar readings using standard insulin injection treatment. A blood sugar level less than 140 mg/dL (7.8 mmol/L) is normal. A reading between 140 and 199 mg/dL (7.8 mmol/L and 11.0 mmol/L) indicates prediabetes. A reading of 200 mg/dL (11.1 mmol/L) or higher after two hours suggests diabetes. As illustrated in FIG. 1A, spikes in blood glucose levels above 200 mg/dL occur throughout the day, triggering administration of insulin, which causes the blood glucose level to dramatically drop. Administration of insulin can cause the patient's blood glucose level to drop below 60 mg/dL, which can also be dangerous. When this occurs the patient is alerted to eat, which may result in a blood glucose spike as illustrated in FIG. 1B.

Figure 1C:
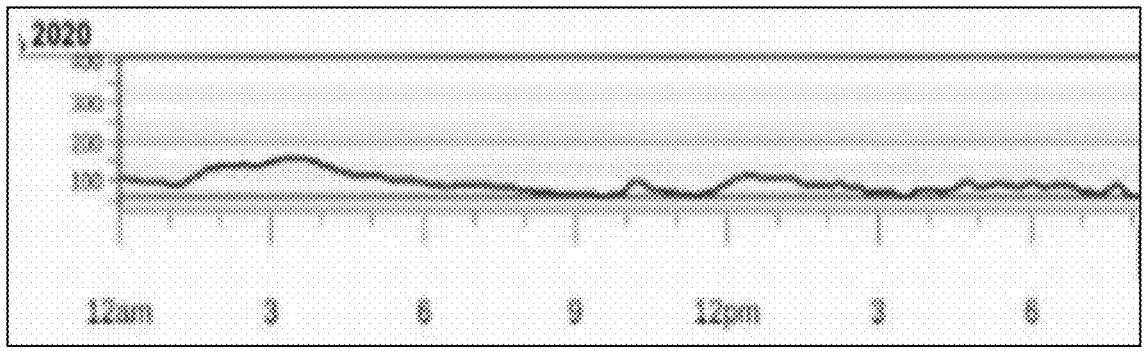
FIG. 1C is a chart showing glucose levels of a diabetic patient after administration of the compositions of the invention.
Figure 1D:
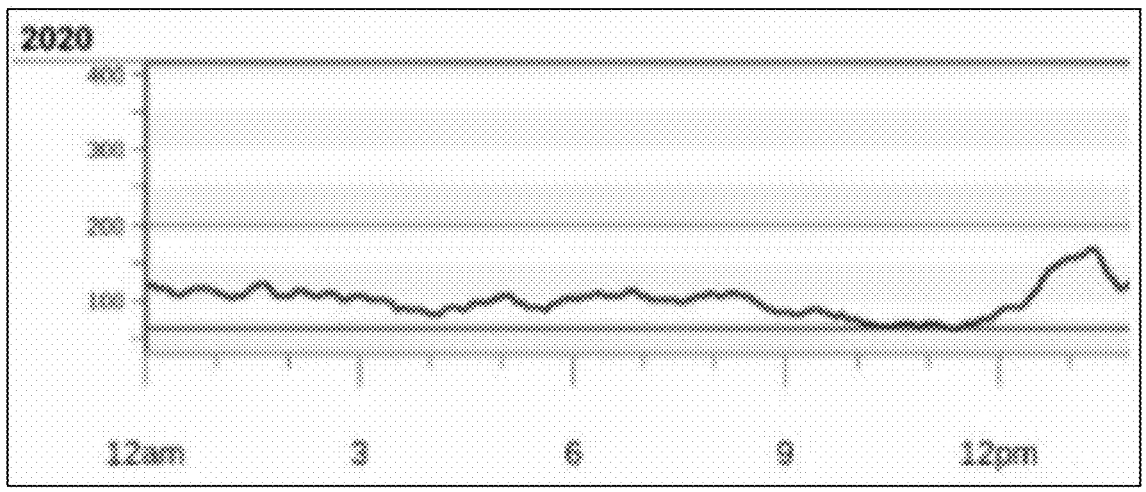
FIG. 1D is a chart showing glucose levels of a diabetic patient after administration of the compositions of the invention.

FIG. 1C and FIG. 1D show the same patient's blood sugar readings while being treated with the CBD and promoter composition. As illustrated in FIG. 1C, blood glucose levels remain constant with normal slight spikes and drops in glucose levels. The patient's blood glucose levels did not rise above 200 mg/dL or drop below 60 mg/dL at any point during an eight month course of treatment.

Example 2

A female diabetes patient aged 90 years was administered the tincture once per day orally following a heart attack. The patient was provided no other form of treatment following the heart attack. TABLE 3 is the results of renal blood panels that were taken 3 months prior to the heart attack (<3 months) and 3 months following the heart attack (>3 Months):

TABLE 3

| Renal Panel | Normal Range | | <3 Months | >3 Months | % Change |
|---|---|---|---|---|---|
| Sodium | 136-145 | mmol/L | 142 | 144 | +1.4 |
| Potassium | 3.5-5.1 | mmol/L | 4.1 | 4.0 | -2.4 |
| Chloride | 98-107 | mmol/L | 103 | 109 | +5.8 |
| Carbon Dioxide | 21-32 | mmol/L | 31 | 30 | -3.2 |
| Glucose | 70-99 | mg/dL | 127 | 102 | -19.7 |
| BUN | 7-18 | mg/dL | 41 | 15 | -63.4 |
| Creatinine | 0.6-1.0 | mg/dL | 2.1 | 1.7 | -19.0 |
| Albumin | 3.4-5.0 | g/dL | 3.0 | 3.2 | +6.7 |
| Calcium | 8.5-10.2 | mg/dL | 9.1 | 9.2 | +1.1 |
| Phosphate | 2.5-4.9 | mg/dL | 5.1 | 3.9 | -23.5 |
| eGFR | >60 | ml/Min/1 | 24 | 30 | +25 |

Notably, the patient shows a 19.7% reduction (127 to 102) in fasting glucose blood levels. Older, long term diabetic patients do not generally exhibit a reduction in blood glucose levels following a heart attack. In fact, blood glucose levels typically rise in non-diabetic patients following heart attacks, suggesting that the tincture has a profound effect on blood glucose levels.

The patient shows dramatic improvement in kidney function as well, as indicated by increased estimated glomerular filtration rate (eGFR) and decreases in blood urea nitrogen (BUN) and creatinine levels. Heart disease has long been associated with kidney disease and malfunction. Improvement in kidney function is not typically seen following heart attacks in older patients.

Example 3

Figure 2A:
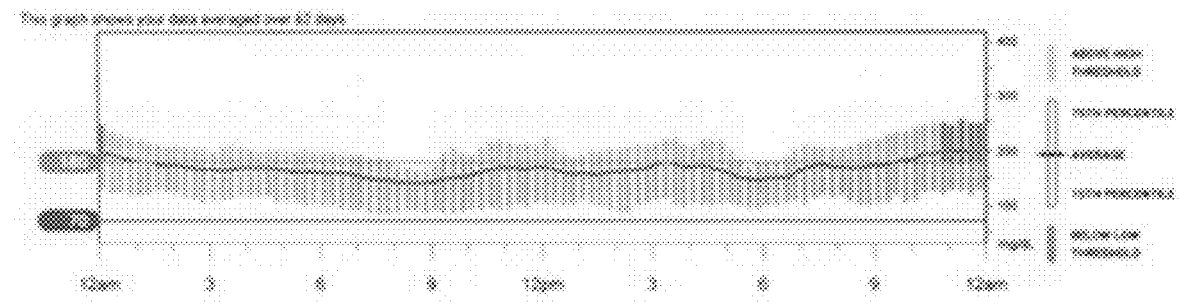
FIG. 2A is a chart showing glucose levels of a diabetic patient before administration of the compositions of the invention.

A 5 year old, female type 1 diabetes patient was administered a tincture containing isolated CBD sublingually. Blood sugar levels were recorded every 5 minutes 24 hours a day. FIG. 2A is a 24 hour blood glucose cycle acquired before the patient was administered the tincture that represents the patient's daily blood glucose level cycle while being treated with daily injections of low-dose insulin. The patient's average glucose level was 167 mg/dL (average is 70-180 mg/dL), with blood glucose levels outside the normal range for almost 40% of the day, and an A1c level of 7.3% (normal is 5.0% to 5.5%). The patient also exhibited nighttime spikes in blood sugar to very high levels prior to treatment with the tincture and despite insulin treatment.

Figure 2B:
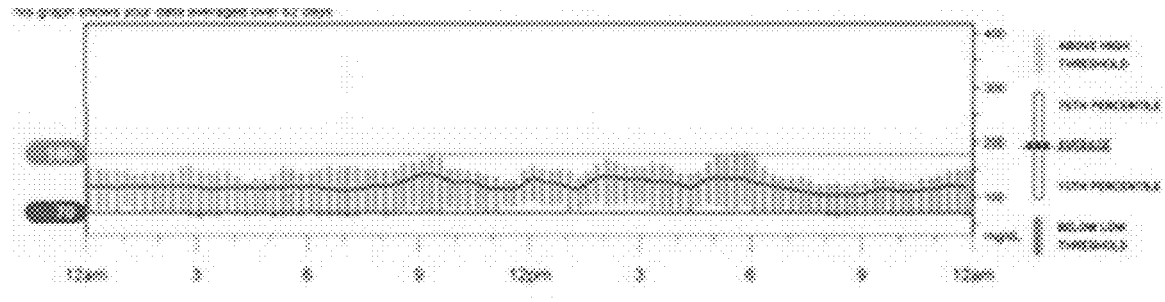
FIG. 2B is a chart showing glucose levels of a diabetic patient 60 days after beginning treatment with the compositions of the invention.

FIG. 2B shows the patient's blood sugar readings over a 24 hour period 60 days after starting treatment with the tincture. Notably, the patient's average glucose level was reduced to 121 mg/dL with levels outside of the normal range 14% of the day. A1c levels were also lower, 6.2%, and the nighttime blood sugar spikes were eliminated. Basal insulin treatment was maintained with the same daily injections of low-dose insulin as the previous test.

Figure 2C:
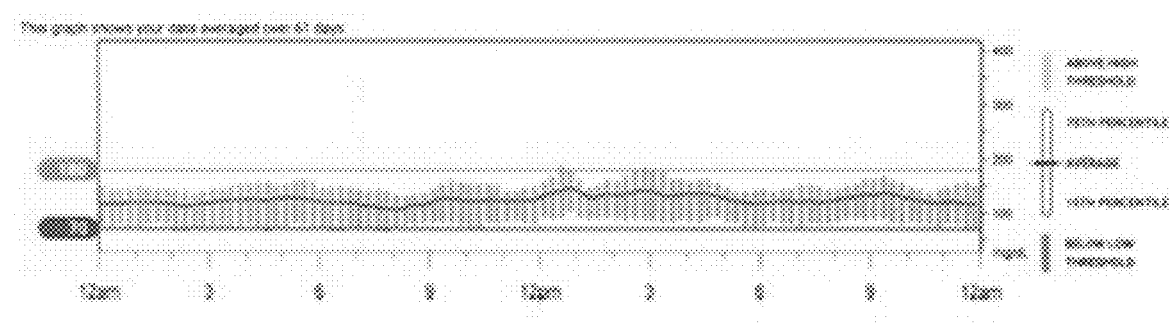
FIG. 2C is a chart showing glucose levels of a diabetic patient 3 months after beginning treatment with the compositions of the invention.

FIG. 2C shows the patient's blood sugar readings over a 24 hour period 3 months after starting treatment with the tincture. The patient's average glucose level, 124 mg/dL, and A1c levels, 6.3%, are consistent with the previous readings, see FIG. 2, with levels outside of the normal range 13% of the day. No nighttime blood sugar spikes were observed. Basal insulin treatment was maintained with the same daily injections of low-dose insulin as the previous test.

The invention claimed is:

1. A composition comprising:
   a cannabidiol in an amount of 0.5% by weight to 50% by weight based on total weight of the composition;
   quercetin in an amount of 0.01% by weight to 5% by weight based on total weight of the composition; and
   zinc in an amount of 0.01% by weight to 5% by weight, based on total weight of the composition.

2. The composition of claim 1, wherein the cannabidiol comprises a cannabidiol analog and/or a cannabidiolic acid.

3. The composition of claim 1, wherein the composition further comprises an anti-inflammatory compound, an antibiotic, a plant extract, a mineral in addition to the zinc, a mineral salt in addition to a zinc salt, a vitamin, an amino acid, a peptide, a protein, cyanobacteria, green algae, an antioxidant, or combinations thereof.

4. The composition of claim 3, wherein the concentration of the anti-inflammatory compound, the antibiotic, the plant extract, the mineral in addition to the zinc, the mineral salt in addition to a zinc salt, the vitamin, the amino acid, the peptide, the protein, the cyanobacteria, the green algae, the antioxidant, or combinations thereof is about 0.01 wt. % to about 5 wt. %, relative to the total amount of the composition.

5. The composition of claim 1, wherein the composition is in the form of a cream, liniment, ointment, lotion, tincture, tonic, tablet, capsule or combinations thereof.

6. A method for treating diabetes comprising administering a therapeutically effective amount of the composition of claim 1 to a patient in need of treatment.

7. The method of claim 6, wherein the cannabidiol comprises a cannabidiol analog and/or a cannabidiolic acid.

8. The method of claim 6, wherein the therapeutically effective amount of a cannabinoid is about 2 milligrams of cannabinoid per kilogram of body weight (mg/kg) to about 10 mg/kg.

9. The method of claim 6, wherein administering comprises topically applying the composition to the skin.

10. The method of claim 6, wherein administering comprises orally administering the composition.

11. The method of claim 6, wherein the composition further comprises an anti-inflammatory compound, an antibiotic, a plant extract, a mineral in addition to the zinc, a mineral salt in addition to a zinc salt, a vitamin, an amino acid, a peptide, a protein, cyanobacteria, green algae, an antioxidant, or combinations thereof.

12. The method of claim 6, wherein the composition is in the form of a cream, liniment, ointment, lotion, tincture, tonic, tablet, capsule or combinations thereof.

13. The composition of claim 1, wherein the composition further comprises a plant-derived oil.

14. The method of claim 6, wherein the composition further comprises a plant-derived oil.

* * * * *